(12) United States Patent
Liang et al.

(10) Patent No.: US 7,273,829 B2
(45) Date of Patent: Sep. 25, 2007

(54) CATALYST FOR OXIDATION OF SATURATED AND UNSATURATED ALDEHYDES TO UNSATURATED CARBOXYLIC ACID, METHOD OF MAKING AND METHOD OF USING THEREOF

(75) Inventors: Wugeng Liang, Katy, TX (US); Scott A. Stevenson, Houston, TX (US); Joseph R. Linzer, Houston, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 0 days.

(21) Appl. No.: 11/316,211

(22) Filed: Dec. 22, 2005

(65) Prior Publication Data

US 2007/0149806 A1 Jun. 28, 2007

(51) Int. Cl.
*B01J 23/00* (2006.01)
(52) U.S. Cl. .............. 502/300; 502/240; 502/241; 502/242; 502/243; 502/245; 502/246; 502/247; 502/248; 502/250; 502/263; 502/302
(58) Field of Classification Search .......... 502/300, 502/240, 241, 242, 243, 244, 245, 246, 247, 502/248, 250, 263, 302
See application file for complete search history.

(56) References Cited

U.S. PATENT DOCUMENTS 6,420,307 B1 * 7/2002 Wu et al. ............... 502/300

FOREIGN PATENT DOCUMENTS

| JP | 11179209 | * | 7/1999 |
| JP | 2002233758 | * | 8/2002 |
| JP | 2002292291 | * | 10/2002 |
| JP | 2002306970 | * | 10/2002 |

* cited by examiner

*Primary Examiner*—Johann Richter
*Assistant Examiner*—Chukwuma Nwaonicha
(74) *Attorney, Agent, or Firm*—Jim P. Wheelington

(57) ABSTRACT

The invention is a supported or bound heteropoly acid catalyst composition, a method of making the catalyst composition and a process for the oxidation of saturated and/or unsaturated aldehydes to unsaturated carboxylic acids using the catalyst composition. The catalyst composition has an active heteropoly acid component containing molybdenum, vanadium, phosphorus and cesium and an inert heteropoly acid component containing molybdenum, phosphorus and cesium, potassium, rubidium or sodium at a relative molybdenum:cesium/potassium/rubidium/sodium molar ratio of above about 12:2.

The catalyst is made by dissolving compounds of the components of each of the heteropoly acid compounds in a solution, precipitating the heteropoly acid compounds, contacting the heteropoly acid compounds to form a catalyst precursor and calcining the catalyst precursor to form a heteropoly acid compound catalyst.

Unsaturated aldehydes, such as methacrolein, may be oxidized in the presence of the heteropoly acid compound catalyst to produce an unsaturated carboxylic acid, such as methacrylic acid.

7 Claims, 3 Drawing Sheets

Figure 3

CATALYST FOR OXIDATION OF SATURATED AND UNSATURATED ALDEHYDES TO UNSATURATED CARBOXYLIC ACID, METHOD OF MAKING AND METHOD OF USING THEREOF

BACKGROUND OF THE INVENTION

1. Field of the Invention

This invention relates to supported or bound heteropoly acid catalyst compositions, a method of making such catalyst compositions and a process for the oxidation of unsaturated aldehydes, such as methacrolein, to unsaturated carboxylic acids, such as methacrylic acid, in a vapor phase reaction using such catalyst compositions.

2. Description of the Prior Art

Various catalysts are known for the gas phase catalytic oxidation of unsaturated aldehydes to unsaturated carboxylic acids. Included are molybdenum-based mixed metal oxides compound which can contain oxides of metals such as phosphorus, arsenic, cesium, rubidium, cobalt, nickel, iron, chromium, antimony, tellurium and silicon in addition to molybdenum. These same metals and others may occur in heteropoly acid compounds as metal oxide clusters forming heteropolyoxoanions in acid form instead of simple metal oxides. Heteropoly acid compounds are also known as catalysts for the gas phase catalytic oxidation of unsaturated aldehydes to unsaturated carboxylic acids. Heteropoly acid compounds have a central metal atom surrounded by a framework of other metal atoms connected to each other and the central metal atom through oxygen atoms. The central metal atom is different ("hetero") from the framework metal atoms.

U.S. Pat. No. 3,998,876 discloses a catalyst of a heteropoly acid compound containing phosphorus, molybdenum, arsenic, at least one of vanadium, tungsten, copper, iron, manganese or tin, at least one of lithium, sodium, potassium, rubidium or cesium and ammonium groups in the form of a salt of the heteropoly acid. The examples of the nonsupported catalyst were shown to have a higher degree of conversion at comparable selectivities compared to a catalyst supported on an alumina/silica carrier.

U.S. Pat. No. 4,320,227 discloses a heteropoly acid catalyst containing molybdenum, vanadium, phosphorus, one or more of copper, tin, thorium, aluminum, germanium, nickel, iron, cobalt, zinc, titanium, lead, rhenium, zirconium, cerium, chromium, bismuth or arsenic, and one or more of potassium, rubidium, cesium or thallium. For improvements in thermal stability and catalyst life and increase in yield of methacrolein and methacrylic acid a suitable carrier, such as silicon carbide, α-alumina, aluminum powder, diatomaceous earth or titanium oxide, can be used. Active carriers which react with heteropoly acids are not preferable.

U.S. Pat. No. 5,191,116 discloses a heteropoly acid catalyst containing molybdenum, vanadium and/or copper, phosphorus and/or arsenic, at least one of an alkali metal, such as lithium sodium, potassium, rubidium, and cesium, an alkaline earth metal, such as magnesium, calcium, strontium and barium, or thallium and at least one of silver, zinc, cadmium, titanium, zirconium, niobium, tantalum, chromium, tungsten, manganese, iron, cobalt, nickel, boron, aluminum, germanium, rhodium, tin, antimony, bismuth, selenium, tellurium, yttrium, lanthanum, cerium, praseodymium and neodymium. The catalysts may be carried on a carrier, such as silica, α-alumina, titania, zirconia, diatom earth, silica alumina, water soluble silica sol and silicon carbide. Inert carriers having a vast plurality of macropores and high porosity are preferred. One working example used a carrier of silica.

Heteropoly acid compounds which are active catalysts generally lack thermal stability. High temperatures will decompose the heteropoly acid structure. Heteropoly acid compounds also generally lack mechanical stability. Their framework structure is inherently fragile and lack of mechanical and thermal strength is a typical characteristic of heteropoly acid compounds. Supporting or binding the heteropoly acid compound to improve mechanical and thermal strength can result in decreased catalyst performance. It would be advantageous to have a supported or bound heteropoly acid compound with increased mechanical and thermal strength without loss of catalyst performance.

One solution to address thermal stability is found in U.S. Pat. No. 5,618,974 which discloses a catalyst for producing methacrylic acid by oxidation of methacrolein, isobutyl aldehyde or isobutyric acid which contains (A) a composite oxide which may be a heteropoly acid of molybdenum, phosphorus, at least one element of arsenic, antimony, germanium, bismuth, zirconium, cerium or selenium, at least one element of cooper, iron, chromium, nickel, manganese, cobalt, tin, silver, zinc, palladium, rhodium or tellurium, at least one of vanadium, tungsten, or niobium and at least one of alkali metals, alkaline earth metals or thallium and (B) a solid acid having acid strength (Ho) of no more than −11.93.

Supported heteropoly acid compounds are used in processes other than gas phase catalytic oxidation of unsaturated aldehydes to unsaturated carboxylic acids.

U.S. Pat. No. 5,990,348 discloses a process for converting alkanes, such as propane or isobutane, to unsaturated carboxylic acids, such as acrylic acid or methacrylic acid, with an oxidizing agent and a heteropoly acid supported on an insoluble polyoxometallate salt, both acid and salt having a polyhedral cage structure or framework. The support can be a cesium salt of a heteropoly acid. The heteropoly acid is water soluble.

U.S. Pat. No. 6,043,184 discloses a process for converting alkanes, such as propane and isobutane, to unsaturated carboxylic acids, such as acrylic acid and methacrylic acid, with an oxidizing agent and a heteropoly acid supported on a porous cesium polyoxometallate salt. The heteropoly acid is water soluble.

SUMMARY OF THE INVENTION

The present invention is for a heteropoly acid catalyst composition, a method of making the catalyst composition and a process of using the catalyst composition for the oxidation of unsaturated aldehydes, such as methacrolein, to unsaturated carboxylic acids, such as methacrylic acid, in a vapor phase reaction. The catalyst composition has an active heteropoly acid component and an inert heteropoly acid component. The active heteropoly acid component has the general formula $Mo_{12}V_aP_bCs_cO_x$ where Mo is molybdenum, V is vanadium, P is phosphorus, Cs is cesium, O is oxygen, a is 0.01 to 5.0, b is 0.5 to 3.5, c is 0.01 to 2.0 and x satisfies the valences. This catalyst composition is essentially insoluble in water. It is bound with or supported on another heteropoly acid compound having the general formula $Mo_{12}P_{b'}M_{c'}O_{x'}$, where Mo is molybdenum, P is phosphorus, M is cesium, potassium, rubidium or sodium, 0 is oxygen, b' is 0.5 to 3.5, c' is greater than 2 and x' satisfies the valences. Preferably, M is cesium, potassium or rubidium, more preferably cesium, and c' is about 2.0 to about 6.0, more preferably about 3.

In general, the method of making the catalyst is to dissolve compounds of the catalyst components of the heteropoly acid compound in an acidified aqueous solution, precipitating particles of the catalyst precursor, drying the solid particles and calcining the solid particles.

In general, the process of using the catalyst compositions for the oxidation of unsaturated aldehydes to unsaturated carboxylic acids in a vapor phase reaction is to contact the unsaturated aldehyde, such as methacrolein, with an oxidizing agent, such as air or another oxygen-containing gas, in the presence of the heteropoly acid compound catalyst at conditions to produce an unsaturated carboxylic acid, such as methacrylic acid.

BRIEF DESCRIPTION OF THE DRAWINGS

A more complete appreciation of the invention and many of the attendant advantages thereof will be readily understood by reference to the following detailed description when considered in connection with the accompanying drawings wherein.

DETAILED DESCRIPTION OF THE INVENTION

Heteropoly acid compounds containing molybdenum, vanadium and bismuth are effective as catalysts for the oxidation of unsaturated aldehydes, such as methacrolein, to unsaturated carboxylic acids, such as methacrylic acid, in a vapor phase reaction. The presence of cesium in a heteropoly compound can be beneficial for improvement of thermal strength. However, as the amount of cesium increases, catalyst performance, both activity and selectivity, decreases. At a relative molybdenum:cesium molar ratio of above about 12:2, the catalyst becomes inert for the oxidation of methacrolein to methacrylic acid in a vapor phase reaction. "Inert" in this context means a relative activity (as defined below) of 0.1 or less.

The catalyst of the present invention has an active heteropoly acid component and an inert heteropoly acid component. The active heteropoly acid component has the general formula $Mo_{12}V_aP_bCs_cO_x$ where Mo is molybdenum, V is vanadium, P is phosphorus, Cs is cesium, O is oxygen, a is 0.01 to 5.0, b is 0.5 to 3.5, c is 0.01 to 2.0 and x satisfies the valences.

The active heteropoly acid component may contain additional elements, such as copper, bismuth, boron, antimony, tungsten, cerium, niobium, indium, iron, chromium, cobalt, nickel, manganese, arsenic, silver, zinc, lead, tin, titanium, aluminum, silicon, tantalum, germanium, gallium, zirconium, magnesium, barium and lanthanum. One embodiment of the active heteropoly acid component has the general formula $Mo_{12}V_aP_bCs_cCu_dM'_eM''_fO_x$ where Mo is molybdenum, V is vanadium, P is phosphorus, Cs is cesium, Cu is copper, M' is bismuth and/or boron, M" is one or more of antimony, tungsten, cerium, niobium, indium, iron, chromium, cobalt, nickel, manganese, arsenic, silver, zinc, lead, tin, titanium, aluminum, silicon, tantalum, germanium, gallium, zirconium, magnesium, barium or lanthanum, O is oxygen, a is 0.01 to 5.0, b is 0.5 to 3.5, c is 0.1 to 2.0, d is 0.0 to 1.5, e is 0.0 to 2.0, f is 0.0 to 5.0, and x satisfies the valences.

This catalyst composition is bound with or supported on an inert heteropoly acid compound having the general formula $Mo_{12}P_{b'}M_{c'}O_{x'}$ where Mo is molybdenum, P is phosphorus, M is cesium, potassium, rubidium or sodium, O is oxygen, b' is 0.5 to 3.5, c' is greater than 2 and x' satisfies the valences. Preferably, M is cesium, potassium or rubidium, more preferably cesium, and c' is about 2.0 to about 6.0, more preferably about 3.

The inert heteropoly acid component may also contain additional elements. One embodiment of the inert heteropoly acid component has the general formula $Mo_{12}V_{a'}P_{b'}M_{c'}Cu_{d'}M'_{e'}M''_{f'}O_{x'}$ where Mo is molybdenum, V is vanadium, Cs is cesium, Cu is copper, P is phosphorus, M is cesium, potassium, rubidium or sodium, M' is bismuth and/or boron, M" is one or more of antimony, tungsten, cerium, niobium, indium, iron, chromium, cobalt, nickel, manganese, arsenic, silver, zinc, lead, tin, titanium, aluminum, silicon, tantalum, germanium, gallium, zirconium, magnesium, barium or lanthanum, O is oxygen, a' is 0.0 to 5.0, b' is 0.5 to 3.5, c' is 2.0 to 6.0, d' is 0.0 to 1.5, e' is 0.0 to 2.0, f' is 0.0 to 5.0, and x satisfies the valences.

The methods of making the active heteropoly acid component and the inert support/binder which is also a heteropoly acid compound are similar. Compounds containing the elements of the particular heteropoly acid compound, whether the active heteropoly acid component or the inert heteropoly acid support/binder, are dissolved in a liquid which may be aqueous, aqueous/organic mixtures or organic. The liquid is preferably aqueous. The liquid is acidified to promote dissolution of the compounds. The acid may be organic, such as acetic acid, or inorganic, such as nitric acid. The acidity of the liquid may be completely or partially neutralized by the addition of a base, such as an ammonium-containing compound, e.g. ammonium hydroxide. Precipitation may occur spontaneously as the compounds are mixed together in solution or it may be promoted by heating, cooling or other changes in ambient conditions or by adding a material which will act as a nucleus or "seed" for precipitation of particles. This "seed" material can be a compound containing one or more of the elements of the catalyst composition.

Suitable molybdenum compounds are, but not limited to, ammonium paramolybdate, molybdenum trioxide, molybdenum chloride or mixtures or combinations thereof.

Suitable vanadium components are, but not limited to, ammonium metavanadate, vanadium pentoxide, vanadium chloride or mixtures or combinations thereof.

Suitable phosphorus compounds are, but not limited to, phosphoric acid, ammonium phosphite or mixtures or combinations thereof.

Suitable copper compounds are, but not limited to, copper nitrate, copper chloride or mixtures or combinations thereof.

Suitable bismuth compounds are, but not limited to, bismuth nitrate, bismuth oxide, bismuth chloride or mixtures or combinations thereof.

Suitable boron compounds are, but not limited to, boric acid, boric acid salts, boric oxide, borate esters or mixtures or combinations thereof.

Suitable potassium, rubidium, cesium and sodium compounds are, but not limited to, nitrates, oxides, chlorides or mixtures or combinations thereof.

Suitable antimony, tungsten, cerium, niobium, indium, iron, chromium, cobalt, nickel, manganese, arsenic, silver, zinc, lead, tin, titanium, aluminum, silicon, tantalum, germanium, gallium, zirconium, magnesium, barium and lanthanum compounds are, but not limited to, nitrates, oxides, chlorides or mixtures or combinations thereof.

The active heteropoly acid compound and the inert heteropoly acid compound are brought into contact to form a catalyst precursor. The weight of the active heteropoly acid compound component relative to the weight of the inert heteropoly acid compound component is in the ratio of 1:10 to 10:1, preferably 1:3 to 3:1, more preferably 1:2 to 2:1, most preferably about 1:1.

To obtain a bound or supported heteropoly acid catalyst, the active heteropoly acid compound and the inert heteropoly acid compound may be synthesized separately to dried particles which are mixed together and calcined. Alternatively, the dried particles of one of the heteropoly acid compounds may be added during the synthesis prior to precipitation of the other heteropoly acid compound. For example, the inert heteropoly acid compound may be synthesized to dried particles which are added during the synthesis prior to precipitation of the active heteropoly acid compound. As another alternative, the active heteropoly acid compound and the inert heteropoly acid compound may be synthesized sequentially through the precipitation step in the same reaction vessel and then the mixed particles of both heteropoly acid compounds may be dried and calcined. The present invention includes any synthesis method which produces the active heteropoly acid compound which is supported on or bound with the inert heteropoly acid compound.

One purpose of calcination of the catalyst precursor is to activate the catalyst by obtaining an oxide of the metal components. The catalyst precursor may be calcined at a temperature of above about 350° C. for about 2 to about 12 hours. The calcination may be in two stages, one at a temperature lower than about 350° C. for about 1 to about 8 hours and another at a temperature above 350° C. for about 2 to about 12 hours. Calcination may be done in a high temperature oven or kiln.

The process of using the present invention is to contact feedstock containing saturated and/or unsaturated aldehydes with an oxidizing agent in the presence of the heteropoly acid compound catalyst in a vapor phase reaction at reaction conditions to produce an unsaturated carboxylic acid. In one embodiment of the present invention, the feedstock for this process is an unsaturated aldehyde, such as methacrolein, which is the product of an oxidation reaction of an olefin, such as isobutylene, and may contain a recycle of the oxidation of the unsaturated aldehyde, such as methacrolein, to unsaturated carboxylic acids, such as methacrylic acid. Therefore, the feedstock contains, in addition to unsaturated aldehydes, unreacted reactants, inerts and byproducts, such as water, oxygen, nitrogen, carbon monoxide, carbon dioxide, noble gases, acetone, acetic acid, acrolein, methacrylic acid, isobutylene, and other olefins and saturated and unsaturated hydrocarbons. The concentration of unsaturated aldehydes in the feedstock may vary over a wide range. Examples of the concentration of methacrolein are from about 1 vol. % to about 20 vol. % or from about 2 vol. % to about 8 vol. %.

In another embodiment of the present invention, the feedstock contains products and byproducts from a process for hydroformylation of an olefin, such as propylene, to saturated aldehydes, such as butanals, e.g., butanal and isobutanal or isobutyraldehyde. In another embodiment of the present invention, the feedstock contains a combination of saturated and unsaturated aldehydes in proportions from about 5 wt % to about 95 wt %. Embodiments of the present invention having saturated aldehydes in the feedstock are described in U.S. patent application Ser. Nos. 11/198,124 and 11/189,116 which are hereby incorporated by reference.

The oxidizing agent may be air or another oxygen-containing gas. There may be gases or vapors other than oxygen, such as nitrogen, carbon dioxide, noble gases and steam, in the oxidizing agent. The oxidizing agent may be pure oxygen. In one embodiment of the process of the present invention, the amount of oxygen relative to aldehyde would be from 40% less than stoichiometric to 700% more than stoichiometric on a molar basis, preferably 60% more than stoichiometric to 360% more than stoichiometric on a molar basis. In another embodiment of the process of the present invention in which the aldehyde is methacrolein, the amount of oxygen relative to methacrolein is from about 0.3 to about 4, preferably from about 0.8 to about 2.3 by mole ratio.

The process conditions are at a pressure from about 0 atm to about 5 atm, preferably at about 1 atm, and at a temperature from about 230° C. to about 450° C., preferably 250° C. to about 400° C., more preferably about 250° C. to about 350° C.

The reactor for the process of the present invention may be any reactor for a vapor phase reaction, such as a fixed bed reactor, a fluidized bed reactor or a moving bed reactor.

The invention having been generally described, the following examples are given as particular embodiments of the invention and to demonstrate the practice and advantages thereof. It is understood that the examples are given by way of illustration and are not intended to limit the specification or the claims to follow in any manner.

Active Component 1

Ammonium paramolybdate (46.49 g.) was added to 200 ml de-ionized (DI) water at room temperature. Ammonium meta-vanadate (1.28 g.) was added to the above solution. The mixture was stirred at room temperature and all particles were dissolved. Cesium nitrate (4.28 g.) was added to 25 ml DI water, and the solution was added to the above solution. Phosphoric acid (3.80 g.) dissolved in 6 ml DI water was added to the above solution. Copper nitrate (0.51 g.) was added to 5 ml DI water and the solution obtained was added into the above solution. Nitric acid (70%, 11.32 g.) was added to DI water (30 g.), then 7 ml $NH_4OH$ (28%) followed by bismuth nitrate (5.32 g.) was added to the solution and dissolved. This bismuth nitrate solution was added to the above solution and solid particles were precipitated. The mixture temperature was increased to 95° C. Then, antimony trioxide (2.56 g.) and boric acid (0.68 g.) were added to the above mixture.

The liquid of the mixture was evaporated at 100° C. and the solid particles were dried at 130° C. for 16 hrs and sieved to obtain 20-30 mesh particles. The particles were calcined at 380° C. for 5 hrs under air. A catalyst with composition of $Mo_{12}Cs_{1.0}Bi_{0.5}P_{1.5}Cu_{0.1}V_{0.5}Sb_{0.8}B_{0.5}O_x$ was obtained.

6.0 cc of the calcined material was loaded in the reactor with 9 cc of quartz chips and the reaction is carried out at 15 psia with a vapor steam of the following composition: 4 vol % methacrolein, 8 vol % oxygen and 30 vol % steam with the balance being nitrogen. The following methacrolein conversions and methacrylic acid selectivities were obtained at the specified flowrates and temperatures:

TABLE 1

Conversion and selectivity of Active Component 1

| Flowrate (sccm) | Temperature (C.) | Conversion (%) | Selectivity (%) |
|---|---|---|---|
| 100 | 276 | 64.6 | 84.4 |
| 75 | 281 | 79.3 | 83.6 |
| 50 | 280 | 95.1 | 82.1 |
| 50 | 282 | 96.9 | 80.0 |
| 57 | 283 | 93.8 | 82.8 |

Based on the above catalytic data, the relative activity of Active Component 1 is defined as 2.0 and the relative selectivity of Active Component 1 is defined as 0.0. If a catalyst showed an activity 50% higher than Active Component 1, then this catalyst would have a relative activity 3.0.

It is well known that selectivity for methacrolein oxidation (and indeed most partial oxidation reactions) is dependent on methacrolein conversion, i.e., as conversion is increased the selectivity decreases due to further oxidation of the desired products. Given this, the selectivities of two different catalysts must be compared at the same conversion for the comparison to be meaningful. The selectivity of active component 1 was measured across a wide range of conversions, from about 65% to about 97% and a curve was fit to this data over that range. The actual selectivities of the following Examples were compared to the selectivity curve that was generated for the catalyst of Active Component 1 at the same conversion. The absolute percent difference between the selectivities of the catalysts of the Examples and the selectivity of Active Component 1 at the same conversion is reported in Table I as "relative selectivity." If the catalyst showed a selectivity 1.0% higher than Active Component 1 at the same conversion, then this catalyst would have a relative selectivity of 1.0. The measurement error on the relative selectivity number is roughly ±2. Mass balances were measured for every sample and averaged 97+%.

Support/Binder 1

Ammonium paramolybdate (45.86 g.) was added to 200 ml de-ionized (DI) water at room temperature. Ammonium meta-vanadate (1.27 g.) was added to the above solution. The mixture was stirred at room temperature and all particles were dissolved. Cesium nitrate (12.66 g.) was added to 60 ml DI water, and the solution was added to the above solution. Phosphoric acid (3.74 g.) dissolved in 6 ml DI water was added to the above solution. Copper nitrate (0.50 g.) was added to 5 ml DI water and the solution obtained was added into the above solution. Nitric acid (70%, 11.41 g.) was added to DI water (30 g.), then 7 ml NH$_4$OH (28%) was added into this solution. The solution obtained then was added to the above solution.

The mixture was heated to 100° C. to precipitate solid particles. Liquid was evaporated from the mixture and the solid particles were dried at 130° C. for 16 hrs. Part of the dried material was formed and sieved to obtain 20-30 mesh particles. The particles were calcined at 380° C. for 5 hrs under air. A material with composition of Mo$_{12}$Cs$_{3.0}$P$_{1.5}$Cu$_{0.1}$V$_{0.5}$O$_x$ was obtained.

6.0 cc of the calcined material was loaded in the reactor with 9 cc of quartz chips and the reaction was carried out under the same conditions as Active Component 1. There was little conversion with this material and a relative activity of less than 0.1 was obtained.

EXAMPLE 1

This is an example of a mixture of solid Active Component 1 and solid Support/Binder 1.

50 wt % of the fines after drying of the Support/Binder 1 material and 50 wt % of the fines after drying of the above Active Component 1 were mixed, formed, sized and calcined at 380° C. for five hours under air. A catalyst with composition of 50% of Support/Binder 1 and 50% of the above Active Component 1 was obtained.

6.0 cc of the catalyst was loaded in the reactor with 9 cc quartz chips and tested under the same conditions as Active Component 1. With this catalyst of 50% inert, i.e., about 3 cc Active Component 1 in about 6 cc catalyst composition, a relative activity of 2.8 is obtained, which is higher than the activity obtained with 6 cc of Active Component 1 alone. If the activity is calculated based on the active component content, then the relative activity will be about 5.6. The relative selectivity obtained for this catalyst is 0.0, which is the same as for active component 1 alone.

EXAMPLE 2

This is an example of the support/binder being added in the synthesis solution of the active component.

Ammonium paramolybdate (27.90 g.) was added to 120 ml de-ionized (DI) water at room temperature. Ammonium meta-vanadate (0.77 g.) was added to the above solution. The mixture was stirred at room temperature and all particles were dissolved. Cesium nitrate (2.56 g.) was added to 15 ml DI water, and the solution was added to the above solution. Phosphoric acid (2.28 g.) dissolved in 4 ml DI water was added to the above solution. Copper nitrate (0.30 g.) was added to 4 ml DI water and the solution obtained was added into the above solution. 30 grams of the fines of Support/Binder 1 after drying was added into the above solution. A solution of nitric acid (70%, 6.80 g.) added to DI water (18 g.) was prepared, then 4.2 ml NH$_4$OH (28%) followed by bismuth nitrate (3.19 g.) was added to the solution and dissolved. This bismuth nitrate solution was added to the above mixture. The mixture temperature was increased to 95° C. Then, antimony trioxide (1.54 g.) and boric acid (0.41 g.) were added to above mixture.

The mixture was heated to 100° C. and liquid was evaporated from the mixture. The solid particles were dried at 130° C. for 16 hrs, and sieved to obtain 20-30 mesh particles. The particles were calcined at 380° C. for 5 hrs under air to obtain the catalyst.

If the inert were not added in the above preparation, it is estimated, based on the amounts of raw material used, that 30 grams of catalyst would have been obtained after calcination. It is further estimated that the 30 grams inert material added resulted in 21.6 grams of additional material after calcination. These estimates are from calculations based on the amounts of the reactive components and from empirical observation of weight loss after calcination due to evolution of water and other volatiles, such as nitrates. Based on these estimates, the inert content was about 42% in this example.

6.0 cc of the calcined material was loaded in the reactor with 9 cc quartz chips and the reaction was carried out under the same conditions as Active Component 1. With this supported or bound catalyst (42% inert), a relative activity of 2.5 was obtained, which is higher than the activity obtained with 6 cc of Active Component 1. The activity based on the amount of active component (58%) is 4.3. The relative selectivity obtained for this catalyst is 0.0, which is the same as for Active Component 1 alone.

Active Component 2

(Less Nitric Acid and no NH$_4$OH is Used Here Compared to Active Component 1.)

Ammonium paramolybdate (46.49 g.) was added to 200 ml de-ionized (DI) water at room temperature. Ammonium meta-vanadate (1.28 g.) was added to the above solution. The mixture was stirred at room temperature and all particles were dissolved. Cesium nitrate (4.28 g.) was added to 25 ml DI water, and the solution was added to the above solution. Phosphoric acid (3.80 g.) dissolved in 6 ml DI water was added to the above solution. Copper nitrate (0.51 g.) was added to 5 ml DI water and the solution obtained was added into the above solution. Nitric acid (70%, 4.31 g.) was added to DI water (30 g.), then bismuth nitrate (5.32 g.) was added to the solution and dissolved. This bismuth nitrate solution was added to the above solution. The mixture temperature was increased to 95° C. Then, antimony trioxide (2.56 g.) and boric acid (0.68 g.) were added to the above mixture.

The mixture was heated to 100° C. and liquid was evaporated from the mixture. The solid particles were dried at 130° C. for 16 hrs, and sieved to obtain 20-30 mesh particles. The particles were calcined at 380° C. for 5 hrs under air. A catalyst with composition of Mo$_{12}$Cs$_{1.0}$Bi$_{0.5}$P$_{1.5}$Cu$_{0.1}$V$_{0.5}$Sb$_{0.8}$B$_{0.5}$O$_x$ was obtained.

6.0 cc of the calcined material was loaded in the reactor and the reaction is carried out under the same conditions as Active Component 1. A relative activity of 1.0 and a relative selectivity of 2.0 were obtained.

EXAMPLE 3

This is an example of a supported or bound catalyst with an active component prepared like Active Component 2 and a support or binder of Support/Binder 1 prepared in a method similar to Example 2.

Ammonium paramolybdate (23.25 g.) was added to 100 ml de-ionized (DI) water at room temperature. Ammonium meta-vanadate (0.65 g.) was added to the above solution. The mixture was stirred at room temperature and all particles were dissolved. Cesium nitrate (2.13 g.) was added to 13 ml DI water, and the solution was added to the above solution. Phosphoric acid (1.92 g.) dissolved in 3 ml DI water was added to the above solution. Copper nitrate (0.26 g.) was added to 3 ml DI water and the solution obtained was added into the above solution. 30.0 grams of Support/Binder 1 was added into the above solution. A solution of nitric acid (70%, 2.5 g.) added to DI water (30 g.) was prepared, then bismuth nitrate (2.66 g.) was added to the solution and dissolved. This bismuth nitrate solution was added to the above solution. The mixture temperature was increased to 95° C. Then, antimony trioxide (1.28 g.) and boric acid (0.34 g.) were added to the above mixture.

The mixture was heated to 100° C. and liquid was evaporated from the mixture. The solid particles were dried at 130° C. for 16 hrs, and sieved to obtain 20-30 mesh particles. The particles were calcined at 380° C. for 5 hrs under air.

6.0 cc of the calcined material was loaded in the reactor with 9 cc quartz chips and the reaction is carried out under the same conditions as Active Component 1. With this catalyst of 46% inert material in it, a relative activity of 2.0 and a relative selectivity of 1.0 were obtained, which is higher than the activity of Active Component 2 with 6 cc loading. The relative activity based on the amount of active component is 3.7.

EXAMPLE 4

This is an example of a supported or bound catalyst with an active component prepared like Active Component 2 and with more support/binder content of Support/Binder 1 than Example 3 and prepared in a method similar to Example 2.

Ammonium paramolybdate (11.62 g.) was added to 50 ml de-ionized (DI) water at room temperature. Ammonium meta-vanadate (0.32 g.) was added to the above solution. The mixture was stirred at room temperature and all particles were dissolved. Cesium nitrate (1.07 g.) was added to 6.3 ml DI water, and the solution was added to the above solution. Phosphoric acid (0.98 g.) dissolved in 2 ml DI water was added to the above solution. Copper nitrate (0.13 g.) was added to 2 ml DI water and the solution obtained was added into the above solution. 30.0 grams of Support/Binder 1 was added into the above solution. A solution of nitric acid (70%, 1.2 g.) added to DI water (8 g.) was prepared, then bismuth nitrate (1.33 g.) was added to the solution and dissolved. This bismuth nitrate solution was added to the above solution. The mixture temperature was increased to 95° C. Then, antimony trioxide (0.64 g.) and boric acid (0.17 g.) were added to the above mixture.

The mixture was heated to 100° C. and liquid was evaporated from the mixture. The solid particles were dried at 130° C. for 16 hrs, and sieved to obtain 20-30 mesh particles. The particles were calcined at 380° C. for 5 hrs under air.

6.0 cc of the calcined material was loaded in the reactor with 9 cc quartz chips and the reaction is carried out under the same conditions as Active Component 1. For this supported or bound catalyst with 63.2% inert material, a relative activity of 1.3 was obtained, which is higher than the activity obtained with 6 cc of Active Component 2 loading alone (1.0). The activity based on the active component was 3.5. A relative selectivity of 0.0 was obtained.

Support/Binder 2

Ammonium paramolybdate (45.86 g.) was added to 200 ml de-ionized (DI) water at room temperature. Ammonium meta-vanadate (1.27 g.) was added to the above solution. The mixture was stirred at room temperature and all particles were dissolved. Cesium nitrate (12.66 g.) was added to 60 ml DI water, and the solution was added to the above solution. Phosphoric acid (3.76 g.) dissolved in 6 ml DI water was added to the above solution. Copper nitrate (0.50 g.) was added to 5 ml DI water and the solution obtained was added into the above solution. Nitric acid (70%, 11.41 g.) was added to DI water (30 g.), then 7 ml NH$_4$OH (28%) was added into this solution and the solution obtained then was added to the above solution. The temperature of this mixture was raised to 95° C., then antimony trioxide (2.56 g.) and boric acid (0.68 g.) were added to the above mixture.

The mixture was heated to 100° C. to precipitate solid particles. Liquid was evaporated from the mixture. The solid particles were dried at 130° C. for 16 hrs. This material has the composition: Mo$_{12}$Cs$_{3.0}$P$_{1.5}$Cu$_{0.1}$V$_{0.5}$Sb$_{0.8}$B$_{0.5}$O$_x$.

6.0 cc of the calcined material was loaded in the reactor with 9 cc of quartz chips and the reaction was carried out under the same conditions as Active Component 1. There was little conversion with this material and a relative activity of less than 0.1 was obtained.

Active component 3

Ammonium paramolybdate (69.73 g.) was added to 250 ml de-ionized (DI) water at room temperature. Ammonium meta-vanadate (1.93 g.) was added to the above solution. The mixture was stirred at room temperature and all particles were dissolved. Cesium nitrate (6.42 g.) was added to 35 ml DI water, and the solution was added to the above solution. Phosphoric acid (5.71 g.) dissolved in 9 ml DI water was added to the above solution. Copper nitrate (0.77 g.) was added to 8 ml DI water and the solution obtained was added into the above solution. Nitric acid (70%, 16.98 g.) was added to DI water (45 g.), then 12 ml NH$_4$OH (28%) was added into this solution, and then bismuth nitrate (7.89 g.) was added to the solution and dissolved. This bismuth nitrate solution was added to the above solution. The mixture temperature was increased to 95° C. Then, antimony trioxide (3.84 g.) and boric acid (1.02 g.) were added to the above mixture.

The mixture was heated to 100° C. and liquid was evaporated from the mixture. The solid particles were dried at 130° C. for 16 hrs, and sieved to obtain 20-30 mesh particles. The particles were calcined at 380° C. for 5 hrs under air. A catalyst with composition of $Mo_{12}Cs_{1.0}Bi_{0.5}P_{1.5}Cu_{0.1}V_{0.5}Sb_{0.8}B_{0.5}O_x$ was obtained.

6.0 cc of the calcined material was loaded in the reactor and the reaction is carried out under the same conditions as Active Component 1. A relative activity of 1.7 and a relative selectivity of 0.0 were obtained.

EXAMPLE 5

This is an example of a supported or bound catalyst prepared in a method similar to Example 1 as a mixture of the solid Active Component 3 and the solid Support/Binder 2.

50 wt % of the fines after drying of the Support/Binder 2 material and 50 wt % of the fines after drying of Active Component 2 were mixed, formed, sized and calcined at 380° C. for five hours under air. A catalyst with composition of 50% of Support/Binder 2 and 50% of Active Component 3 was obtained.

6.0 cc of the catalyst was loaded in the reactor with 9 cc quartz chips and tested under the same conditions as Active Component 1. With this catalyst of 50% inert, i.e., about 3 cc Active Component 2, a relative activity of 1.8 is obtained, which is higher than the activity of Active Component 2 alone (1.7). The relative activity based on the active component content was about 3.6. A relative selectivity of 0.0 was obtained.

A summary of the activity and selectivity results from the above examples is given in Table 2 below.

TABLE 2

Activity of catalysts with $Cs_3$ material as support/binder

| Example | Active Component | Active Component Relative Activity | Support/ Binder | Support/ Binder Relative Activity | Catalyst Preparation (active component % + support/binder %) | Relative Catalyst Activity*** | | | Relative Catalyst Selectivity |
|---|---|---|---|---|---|---|---|---|---|
| | | | | | | Math Sum | Total Wt. Basis | Active Wt. basis | |
| 1 | 1 | 2.0 | 1 | <0.1 | Method 1* (50% + 50%) | 1.1 | 2.8 | 5.6 | 0.0 |
| 2 | 1 | 2.0 | 1 | <0.1 | Method 2** (58% + 42%) | 1.2 | 2.5 | 4.3 | 0.0 |
| 3 | 2 | 1.0 | 1 | <0.1 | Method 2** (54% + 46%) | 0.6 | 2 | 3.7 | 1.0 |
| 4 | 2 | 1.0 | 1 | <0.1 | Method 2** (36.8% + 63.2%) | 0.4 | 1.3 | 3.5 | 0.0 |
| 5 | 3 | 1.7 | 2 | <0.1 | Method 1* (50% + 50%) | 0.9 | 1.8 | 3.6 | 0.0 |

*Method 1: The catalyst was prepared by mixing the solid active component with the solid support/binder before calcination.
**Method 2: The catalyst was prepared by adding the support/binder to the synthesis solution of the active component.
***Relative catalyst activity:
"Math Sum" is the mathematical summation of the relative activity of active component with the relative activity of the support/binder based on the composition of the catalyst (active component % + support/binder %)
"Total Wt. Basis" is the experimental measurement of relative activity of the complete catalyst (active component and support/binder)
"Active Wt. Basis" is the relative activity based only on the active component of the catalyst (active component %)

It can be seen from the data in Table 1 that the activity is enhanced significantly with the present invention while at least maintaining if not improving selectivity.

EXAMPLES 6-8

Active Component 4 is an Unsupported Catalyst made by the Following Procedure:

Ammonium paramolybdate (46.49 g.) was added to 200 ml de-ionized (DI) water at room temperature. Ammonium meta-vanadate (1.28 g.) was added to the above solution. The mixture was stirred at room temperature and all particles were dissolved. Cesium nitrate (4.28 g.) was added to 25 ml DI water, and the solution was added to the above solution. Phosphoric acid (3.80 g.) dissolved in 6 ml DI water was added to the above solution. Copper nitrate (0.51 g.) was added to 5 ml DI water and the solution obtained was added into the above solution. Nitric acid (70%, 4.30 g.) was added to DI water (30 g.), and then bismuth nitrate (5.32 g.) was added to the solution and dissolved. This bismuth nitrate solution was added to the above solution. The mixture temperature was increased to 95° C. Then, antimony trioxide (2.56 g.) and boric acid (0.68 g.) were added to the above mixture.

The mixture was heated to 100° C. and liquid was evaporated from the mixture. The solid particles were dried at 130° C. for 16 hrs, and sieved to obtain 20-30 mesh particles.

For each Example, a catalyst with composition of $Mo_{12}Cs_{1.0}Bi_{0.5}P_{1.5}Cu_{0.1}V_{0.5}Sb_{0.8}B_{0.5}O_x$ was obtained but the unsupported catalyst precursors were calcined under different temperatures. One portion of particles was calcined at 380° C. (Example 6), another portion of particles was calcined at 415° C. (Example 7) and another portion of particles was calcined at 425° C. (Example 8), all for 5 hrs under air. XRD data for these catalysts after calcination are shown in FIG. 1.

Figure 1:
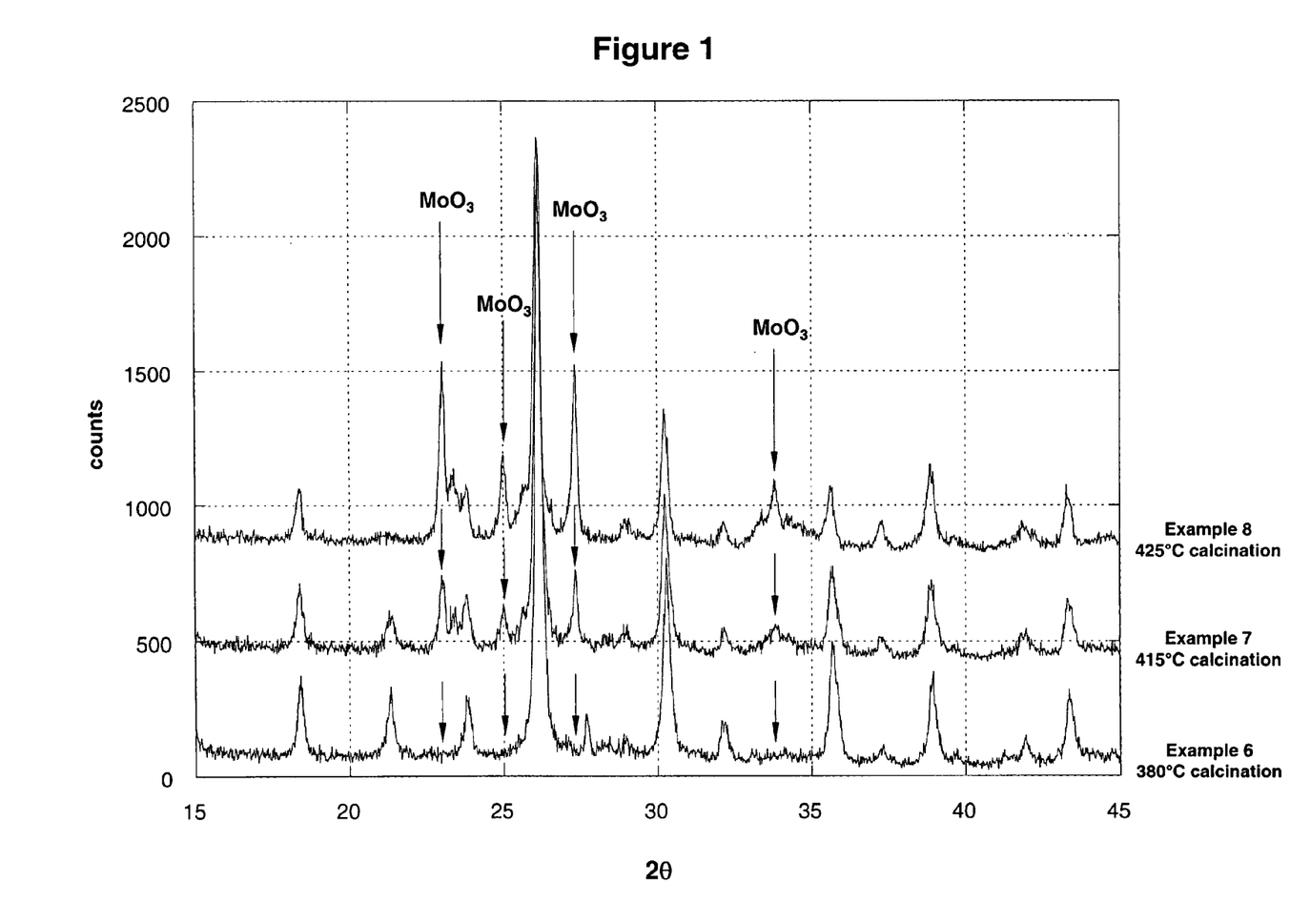
FIG. 1 shows X-ray diffraction of unsupported catalysts calcined at 380° C., 415° C. and 425° C. (Examples 6-8).

For Example 6 (380° C. calcination temperature), there is no structure damage observed, i.e., no $MoO_3$ is formed, as evidenced by the XRD patterns shown in FIG. 1. For Example 7 (415° C. calcination temperature) some damage is observed, evidenced by the formation of $MoO_3$. For Example 8 (425° C. calcination temperature) more $MoO_3$ is observed.

EXAMPLES 9-10

Figure 2:
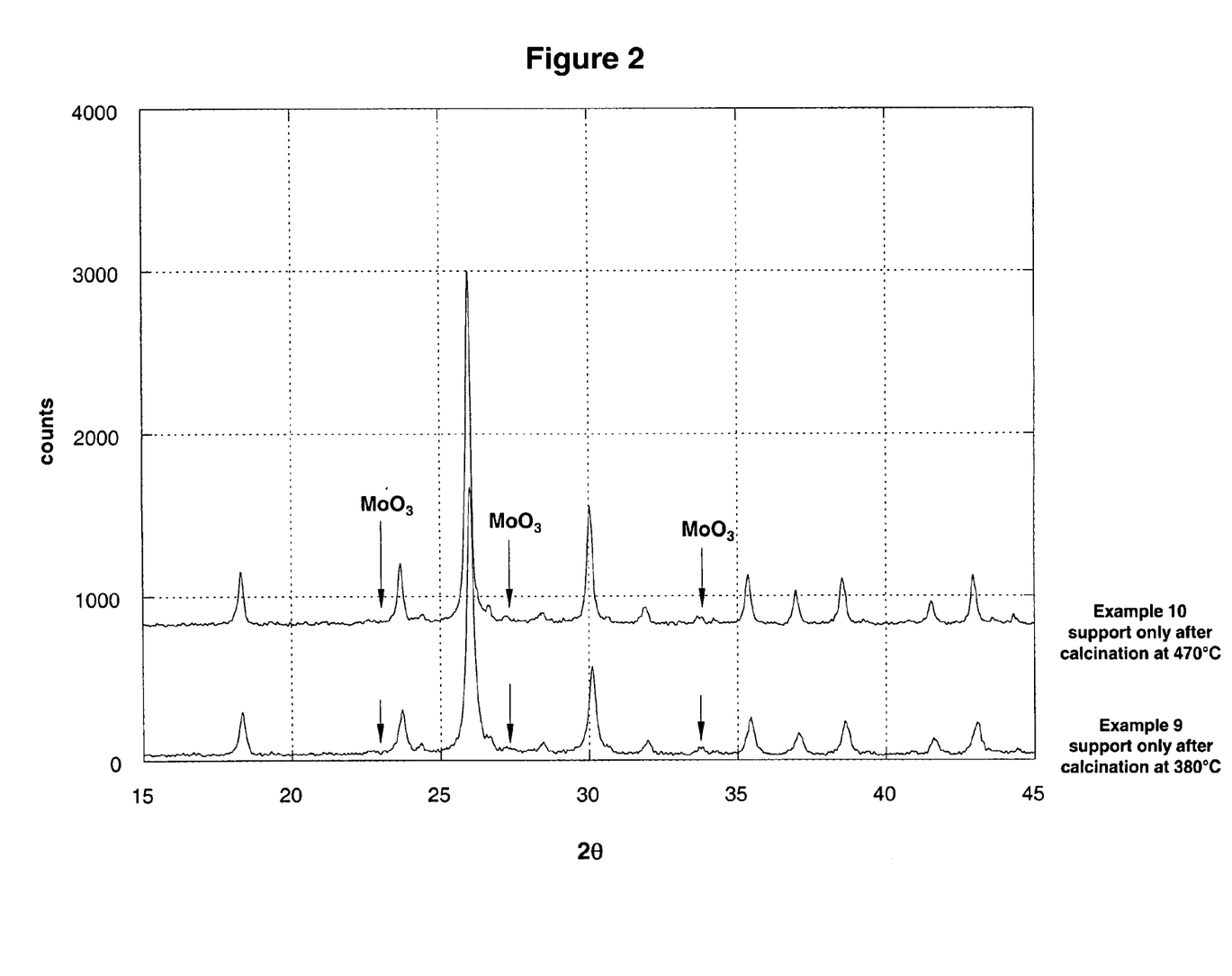
FIG. 2 shows X-ray diffraction of support/binder calcined at 380° C. and 470° C. (Examples 9-10).

A portion of the particles of Support/Binder 1 was calcined at 470° C. (Example 10), higher by 90° C. than the calcination temperature used in the preparation above (Example 9). As shown in FIG. 2, there is no significant degradation of the Keggin structure as evidenced by the minimal formation of $MoO_3$ which demonstrates thermal stability over this temperature range.

EXAMPLE 11

Figure 3:
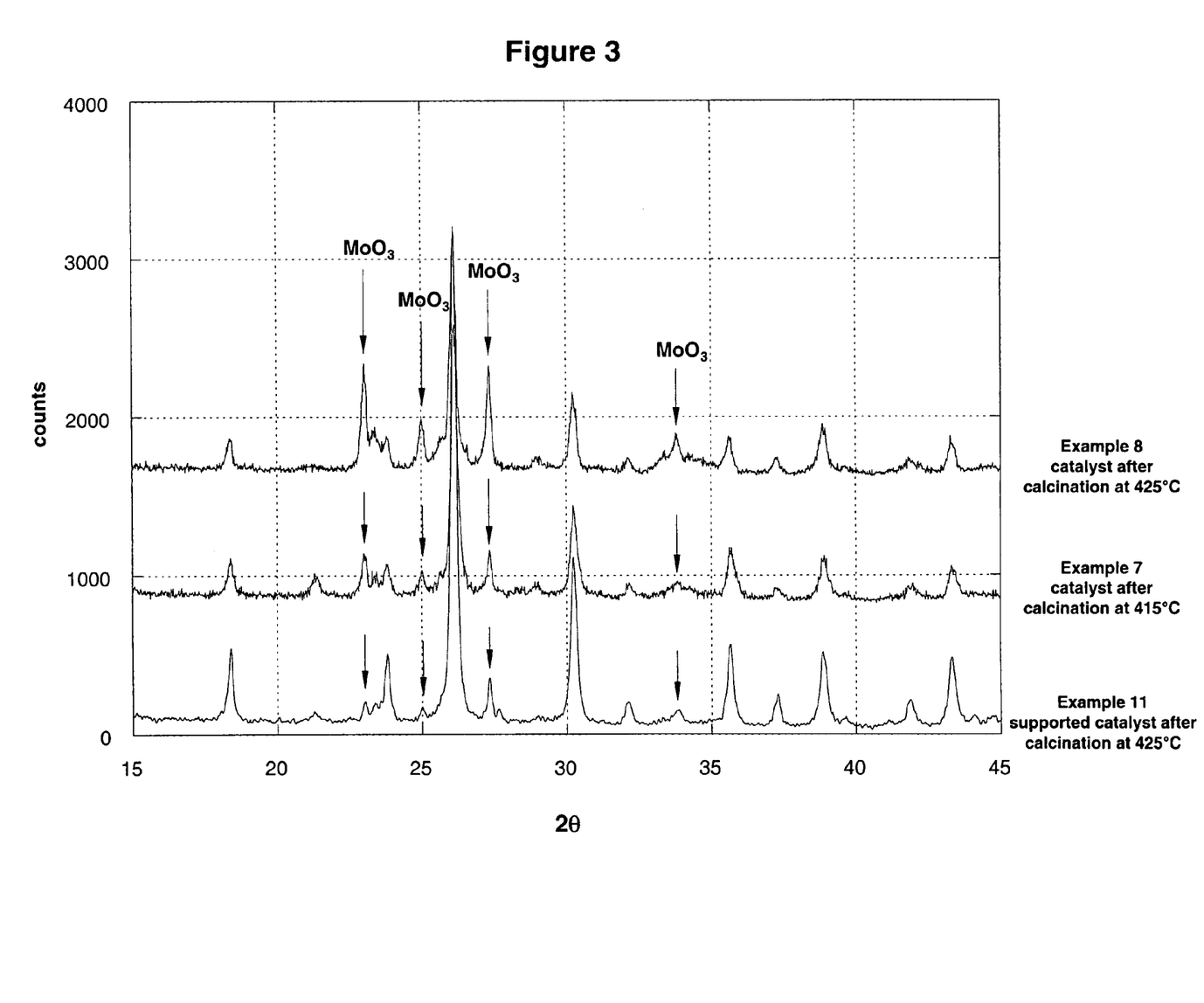
FIG. 3 shows X-ray diffraction of supported or bound catalyst calcined at 425° C. and unsupported catalysts calcined at 415° C. and 425° C. (Example 11 and Examples 7 and 8)

The supported or bound catalyst precursor of Example 2 as described above was calcined at 425° C. As shown in FIG. 3, the $MoO_3$ formed for this supported or bound catalyst is much less than that for Example 8 (unsupported, 425° C. calcination temperature) and even less than that of Example 7 (unsupported, 415° C. calcination temperature). This result clearly indicates that the thermal stability of the supported or bound material is higher than that of the unsupported materials.

In addition to the thermal strength, the mechanical strength is also increased with the binder or support of the present invention. Catalyst components of Example 3 were tested for mechanical strength. Pellets of cylindrical form of the same diameter of the active component, (active component 2), the support/binder (Support/Binder 1) and the catalyst (Example 3) were prepared. The mechanical strength was measured by applying force (F) along the side of the cylinders. The crush strength (C) is calculated based on the length of the pellet (L):

$$C=F/L$$

The relative crush strength (RC) is calculated based on the crush strength of the active component 2, which is defined as RC=1.0. The experimental data of relative crush strength of pellets made of above catalysts are shown in Table 3.

TABLE 3

| The relative crush strength of Example 3 and materials used for making it | |
|---|---|
| Catalyst pellet | Relative crush strength (RC) |
| Active component 2 | 1.0 |
| Support/Binder 1 | 2.5 |
| Example 3 | 1.7 |

The above data show that the crush strength of a supported or bound heteropoly acid compound catalyst having an active heteropoly acid component bound to or supported on an inert heteropoly acid component is improved over that for the active component alone.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letter of patent of the United States of America is:

1. A supported or bound heteropoly acid compound catalyst comprising:
    a) an active heteropoly acid compound of the general formula:

$Mo_{12}V_aP_bCs_cO_x$ where Mo is molybdenum, V is vanadium, P is phosphorus, Cs is cesium, O is oxygen, a is 0.01 to 5.0, b is 0.5 to 3.5, c is 0.01 to 2.0 and x satisfies the valences;
    b) an inert heteropoly acid compound of the general formula:

$Mo_{12}P_{b'}M_{c'}O_{x'}$ where Mo is molybdenum, P is phosphorus, M is cesium, potassium, rubidium or sodium, O is oxygen, b' is 0.5 to 3.5, c' is greater than 2 and x satisfies the valences; wherein the inert heteropoly acid compound is a support or binder for the active heteropoly acid compound.

2. The catalyst of claim 1 wherein the active heteropoly acid compound is brought into contact with the inert heteropoly acid compound to form a supported heteropoly acid catalyst precursor prior to calcining the supported heteropoly acid catalyst precursor to form a supported heteropoly acid compound catalyst.

3. The catalyst of claim 1 wherein the active heteropoly acid compound is of the general formula:

$Mo_{12}V_aP_bCs_cCu_dM'_eM''_fO_x$ where Mo is molybdenum, V is vanadium, P is phosphorus, Cs is cesium, Cu is copper, M' is bismuth and/or boron, M" is one or more of antimony, tungsten, cerium, niobium, indium, iron, chromium, cobalt, nickel, manganese, arsenic, silver, zinc, lead, tin, titanium, aluminum, silicon, tantalum, germanium, gallium, zirconium, magnesium, barium or lanthanum, O is oxygen, a is 0.01 to 5.0, b is 0.5 to 3.5, c is 0.1 to 2.0, d is 0.0 to 1.5, e is 0.0 to 2.0, f is 0.0 to 5.0, x satisfies the valences, and the inert heteropoly acid component has the general formula:

$Mo_{12}V_{a'}P_{b'}M_{c'}Cu_{d'}M'_{e'}M''_{f'}O_{x'}$ where Mo is molybdenum, V is vanadium, Cs is cesium, Cu is copper, P is phosphorus, M is cesium, potassium, rubidium or sodium, M' is bismuth and/or boron, M" is one or more of antimony, tungsten, cerium, niobium, indium, iron, chromium, cobalt, nickel, manganese, arsenic, silver, zinc, lead, tin, titanium, aluminum, silicon, tantalum, germanium, gallium, zirconium, magnesium, barium or lanthanum, O is oxygen, a' is 0.0 to 5.0, b' is 0.5 to 3.5, c' is 2.0 to 6.0, d' is 0.0 to 1.5, e' is 0.0 to 2.0, f' is 0.0 to 5.0, and x satisfies the valences.

4. The catalyst of claim 1 wherein the weight of the active heteropoly acid compound component relative to the weight of the inert heteropoly acid compound component is in the ratio of 1:10 to 10:1.

5. The catalyst of claim 4 wherein the ratio is 1:3 to 3:1.

6. The catalyst of claim 5 wherein the ratio is 1:2 to 2:1.

7. The catalyst of 1 wherein the supported or bound heteropoly acid compound catalyst is water insoluble.

* * * * *